(12) United States Patent
Gidon et al.

(10) Patent No.: US 8,820,141 B2
(45) Date of Patent: Sep. 2, 2014

(54) GAS DETECTION DEVICE

(75) Inventors: Serge Gidon, La Murette (FR); Patrick Chaton, Theys (FR); Sergio Nicoletti, Sinarc (FR)

(73) Assignee: Commissariat a l'energie Atomique et aux Energies Alternatives, Paris (FR)

( * ) Notice: Subject to any disclaimer, the term of this patent is extended or adjusted under 35 U.S.C. 154(b) by 800 days.

(21) Appl. No.: 12/909,487

(22) Filed: Oct. 21, 2010

(65) Prior Publication Data
US 2011/0094291 A1   Apr. 28, 2011

(30) Foreign Application Priority Data
Oct. 23, 2009  (FR) ...................................... 09 05119

(51) Int. Cl.
*G01N 21/17*   (2006.01)
(52) U.S. Cl.
USPC ........................................ 73/24.02; 73/24.06
(58) Field of Classification Search
USPC .................................. 73/24.01, 24.02, 24.06
See application file for complete search history.

(56) References Cited

U.S. PATENT DOCUMENTS

| | | | | |
|---|---|---|---|---|
| 5,003,815 | A * | 4/1991 | Martin et al. .................... | 73/105 |
| 5,270,214 | A * | 12/1993 | Sessler et al. .................... | 436/94 |
| 5,333,495 | A * | 8/1994 | Yamaguchi et al. ............ | 73/105 |
| 6,202,470 | B1 * | 3/2001 | Chou ........................... | 73/24.02 |
| 6,312,959 | B1 * | 11/2001 | Datskos ......................... | 436/147 |
| 6,525,307 | B1 * | 2/2003 | Evans et al. ............... | 250/227.16 |
| 7,487,667 | B2 * | 2/2009 | Matsumoto et al. ............ | 73/105 |
| 2005/0180678 | A1 * | 8/2005 | Panepucci et al. ............. | 385/13 |
| 2006/0233483 | A1 * | 10/2006 | Tran et al. ....................... | 385/12 |
| 2006/0284774 | A1 * | 12/2006 | Salsman ........................ | 343/703 |
| 2007/0220978 | A1 * | 9/2007 | Su et al. ........................... | 73/632 |
| 2008/0283755 | A1 * | 11/2008 | Dazzi et al. .................... | 73/105 |

FOREIGN PATENT DOCUMENTS

EP       0 478 410 A1    4/1992

OTHER PUBLICATIONS

Preliminary Search Report and Written Opinion for Application No. FR 0905119 dated May 11, 2010.
Churenkov, A. V., *Silicon Micromechanical Optical Waveguide For Sensing and Modulation*, Sensors and Actuators A57 (1996), pp. 21-27.
Hagleitner, C., et al., *CMOS Single-Chip Gas Detection System Comprising Capacitive, Calorimetric and Mass-Sensitive Microsensors*, IEEE Journal of Solid-State Circuits, vol. 37, No. 12, Dec. 2002, pp. 1867-1878.
Pruessner, M. W. et al., *Micromechanical Resonators with Integrated Optical Waveguides for Sensing Applications*, CTuH5 2005 Conference on Lasers & Electro-Optics (CLEO), pp. 761-763.
Siwak, N. et al., *Indium Phosphide Optical MEMS for Chemical and Biological Sensing*, IEEE, 2006, 2 pages.
Zinoviev, K. et al., *Optical Waveguide Cantilever Actuated by Light*, Applied Physics Letters, 92, 011908, (2008), 3 pages.

* cited by examiner

*Primary Examiner* — Daniel S Larkin
(74) *Attorney, Agent, or Firm* — Alston & Bird LLP

(57) ABSTRACT

Device for detecting a gas having an excitation device for exciting the gas by an electromagnetic wave having a wavelength corresponding approximately to that of the gas; and a detection device for detecting the excitation of the gas, the detection device having a waveguide connected to the excitation device, a part of which forms a movable element designed to be in contact with the gas and capable of being set into vibration by the impact of the excited gas molecules; and a measurement sensor, for measuring the vibration of the element, the measurement sensor and the element forming the detection device.

11 Claims, 5 Drawing Sheets

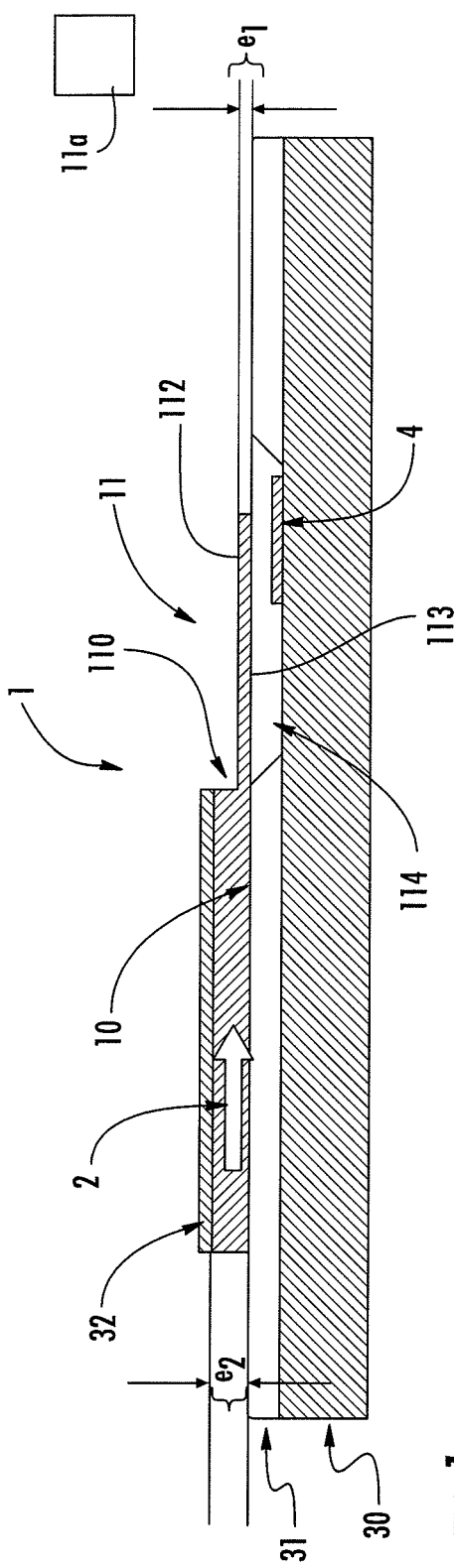
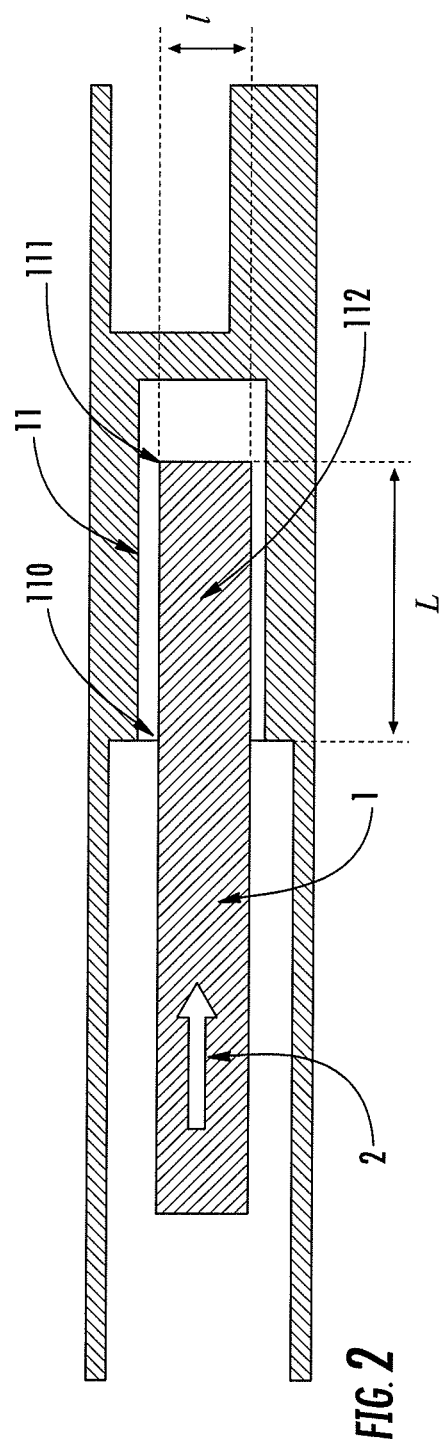

GAS DETECTION DEVICE

FIELD OF THE INVENTION

The invention relates to a gas detection device.

These devices are used in particular for detecting the presence of carbon dioxide, carbon monoxide or methane, so as for example to avoid domestic accidents caused by anoxia.

BACKGROUND

Various gas detection devices are already known.

These may include devices that use physico-chemical absorption processes on a surface (for example, on tin oxide layers), these absorption processes causing a modification in a physical property (for example the number of carriers) of a material. This modification can then be detected in a simple way, for example by electrical conduction.

This type of device is very sensitive. Consequently, it is not very precise as it turns out that it does not necessarily detect the gas presumed to be present. This is because the device may for example be triggered by the moisture of the environment.

Other devices make use of absorption processes on a surface of an organic material having a chemical affinity for the gas to be detected. The detected modification may again be by electrical conduction but also by the variation in the mass of the material using a microbalance.

These devices have a major drawback due to the chemical nature of the interaction. This is because the gas remains trapped in the organic material and, over the course of time, the device losses its sensitivity.

Other devices detect gases using characteristic absorption lines of the gas sought, since gases have well-pronounced spectral signatures in the infrared that allow gases to be distinguished from one another.

The expression "spectral signature of a gas" is understood to mean the absorption spectrum which is specific thereto and which corresponds to dissipation of the light energy after the molecules of the gas have been set in resonance with the wavelength used. Energy is therefore transferred between the light wave and the gas molecules.

Thus, Lidar (Light Detection and Ranging) detection, which consists in detecting the optical scattering echo generated by an absorbent scattering pocket of gas, or photoacoustic detection, which consists in detecting the pressurization of the gas which is heated by the absorption of radiation and which expands within the cavity in which it is placed, may be mentioned.

As regards acoustic detection, the article by C. Hagleitner et al.: "*CMOS single-chip gas detection system comprising capacitive, calorimetric and mass-sensitive microsensors*" published in IEEE Journal of Solid-State Circuits, Vol. 37, No. 12, December 2002 may be mentioned.

In the latter case, the light radiation is absorbed by the molecular bonds of the gas and converted into kinetic energy, thereby resulting, from a macroscopic view point, in the gas being heated up. This heat-up causes a local increase in the pressure, which is detected by means of a membrane, the movement of which is measured.

A device of this type advantageously uses the specificity of the spectral signature of a gas.

However, it does have drawbacks.

Firstly, the sensitivity of the measurement depends on the area of the membrane. Thus, the possibilities of miniaturizing the detection device are considerably limited, if it is desired to obtain reasonable precision.

Secondly, such a device must be used with a closed chamber, especially a tube, in which the gas is made to flow. It is therefore necessary to provide pumping means for making the gas flow into the chamber.

The use of such a device therefore imposes restrictive operating conditions. Thus, this detection device could not be used for domestic purposes.

The object of the invention is to alleviate these drawbacks by providing a device for detecting a gas, which is compact, which ensures precise detection of the gas and which is very simple to use, thereby making domestic applications conceivable.

SUMMARY

In one embodiment, the invention relates to a device for detecting a gas, comprising: excitation means, for exciting said gas by means of an electromagnetic wave having a wavelength corresponding approximately to that of said gas; and detection means, for detecting the excitation of said gas, characterized in that it comprises:

a waveguide connected to said excitation means, a part of which forms a movable element designed to be in contact with said gas and capable of being set into vibration by the impact of the excited gas molecules; and a measurement sensor, for measuring the vibration of said element, said measurement sensor and said element forming said detection means.

Advantageously, the movable element is of the strip type.

In this case, it may also have a comb-type structure that is to say a structure having openings along the length of the element.

Throughout the patent application, the expression "element of the strip type" is understood to mean a flat elongate element, the thickness of which is very much less than its length and the width of which is very much less than its length.

Thus, the width of the element is of the order of the wavelength, its thickness is less than the wavelength and its length is more than 10 times the wavelength.

In a first embodiment, the element is cantilevered at its near or proximal end, its far or distal end being free.

In a second embodiment, the near end and the far end of the element are held fixed.

Preferably, the element has, close to its near end and/or its far end, a slot extending approximately transversely.

Thus, an electromagnetic wave exists at the edge of the element. It is this field that serves to excite the gas. In this configuration, it is the molecules close to the element that will be exited by absorbing the electromagnetic wave, thereby increasing their statistical velocity. The same molecules are then liable to lose this excess energy by striking all the neighbouring surfaces, and in particular those of the movable element.

This is why the thickness of the element is preferably less than that of the rest of the waveguide.

In fact, the intensity of the field around the element will be higher the smaller its thickness.

Advantageously, the waveguide is made of a single material.

As a variant, the element has, on one of its faces, a layer of a material having an index lower than that constituting the waveguide.

Advantageously, the gas excitation means are formed by a laser.

In one particular embodiment of the device, the laser cavity is a ring laser cavity, the waveguide being placed inside the laser cavity.

BRIEF DESCRIPTION OF THE DRAWINGS

The invention will be better understood and other objectives, advantages and features thereof will become more clearly apparent on reading the following description given in conjunction with the appended drawings in which:

FIG. 1 is a side view of an exemplary embodiment of a gas detection device according to the invention;

FIG. 2 is a top view of the device illustrated in FIG. 1;

Figure 3:
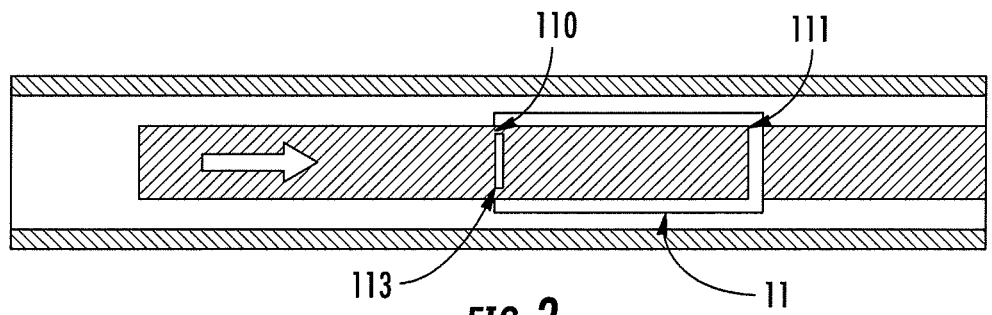
FIG. 3 is a top view of an alternative embodiment of the device illustrated in FIGS. 1 and 2.

The elements common to the various figures will be denoted by the same references.

DETAILED DESCRIPTION

Referring firstly to FIGS. 1 and 2, these illustrate an exemplary embodiment of the gas detection device according to the invention.

This device is placed directly in the environment liable to contain the gas to be detected.

It comprises a waveguide 1 connected, by appropriate means, to excitation means for exciting the gas by means of an electromagnetic wave.

These excitation means are conventionally formed by a laser. The chosen wavelength corresponds approximately to that of the gas intended to be determined.

These excitation means are represented as 11a in FIG. 1.

The electromagnetic wave is represented symbolically by the arrow 2.

As will be described more precisely with regard to FIG. 7a to FIG. 7d, the waveguide 1 is produced from a stack of layers. In this example, the layer 30 is a silicon substrate, the layer 31, called the "sacrificed layer", is made of silica and the waveguide 1 is made of silicon.

The layers 30 and 31 form the support for the waveguide.

Figure 8:
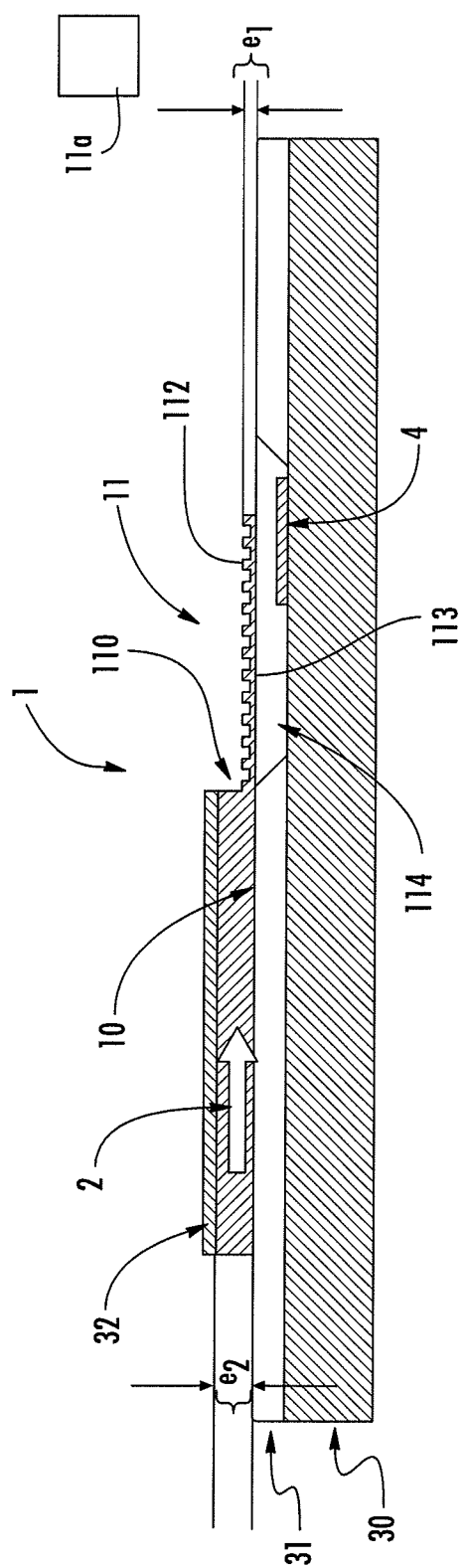
FIG. 8 shows an alternative embodiment of the device of FIG. 1 having a comb type moveable element.

FIGS. 1 and 2 show that the waveguide comprises two differentiated parts: a first part 10 fastened to the support and more particularly to the layer 31 and a second part 11 that forms a movable element of the strip type. FIG. 8 shows a waveguide having a second part 11 that forms a movable element of the comb type.

Specifically, the figures show that, beneath this second part 11, the silica layer 31 has been removed, thereby allowing the part 11 to be free of the support. Thus, the element of the strip type is cantilevered to the support at its near end 110. The two faces 112 and 113 of the element 11 are in contact with the environment containing the gas to be detected.

Embodiments in which substantially only the upper face 112 of the element 11 is in contact with the environment may be envisaged.

Thus, if the free space 114 under the element 11 is reduced, it is essentially the upper face 112 that will be in contact with the gas to be detected.

In operation, the waveguide 1 delivers the electromagnetic field into the environment containing the gas to be detected.

This electromagnetic field supplies energy to the molecules of the gas to be detected and the statistical velocity thereof increases. Consequently, the gas molecules strike the surface of the strip-type element 11. The impact of the gas molecules creates a mechanical impulse on this movable element, setting it into vibration.

The detection device according to the invention also includes means 4 for measuring the vibration.

Different means may be envisaged.

Thus, these means may be a capacitive sensor that electrically analyzes the variation in distance between the element 11 and the substrate 30. Such a sensor is particularly mentioned in the document "*Nanoelectronic and nanomechanical systems*, J. S. Aldridge, *SPIE Proceedings* 2001".

These means may also be based on capacitive detection or on piezoelectric detection, which provide information about the deformation of the movable element. In general, capacitive detection consists in measuring the current that flows across the capacitor formed between the element 11 and the substrate 30, through the action of high-frequency electrical excitation. As regards piezoelectric detection, this consists in measuring the voltage across the terminals of a piezoelectric element deposited on the movable element 11 (or included therein), when this element is deformed. As regards the latter point, the reader may refer to the document "*Ultra-sensitive NEMS-based cantilevers for sensing, scanned probe and very high-frequency applications*", Mo, Li, H. X. Tang and M. L. Roukes, Nature Nanotechnology January 2007.

As shown in FIG. 1, the thickness of the waveguide is advantageously greater in the first part 10 fixed to the support than in the movable element 11.

Of course, the thickness that will be chosen for the waveguide 1 will depend on the wavelength of the electromagnetic wave delivered by the excitation means. In the example given, the detection device is designed to detect $CO_2$ and the wavelength is fixed at about 4.2 μm.

In this case, the thickness $e_1$ of the waveguide at the element 11 is between 0.1 and 1 μm, for example 0.6 μm, whereas the thickness $e_2$ of the first part 10 of the waveguide is between 1 and 2 μm.

To increase the containment of the electromagnetic field in the waveguide in its first part 10, the waveguide may be thickened by providing an additional silica layer 32, the thickness of which is at least 0.5 μm or even around 1 μm.

In general, the thicknesses $e_1$ and $e_2$ of the first and second parts 10 and 11 of the waveguide 1 must be differentiated so as to obtain electromagnetic field containment in the first part 10 and to obtain an electromagnetic field at the edge of the waveguide, in the strip-type element 11.

Figure 4:
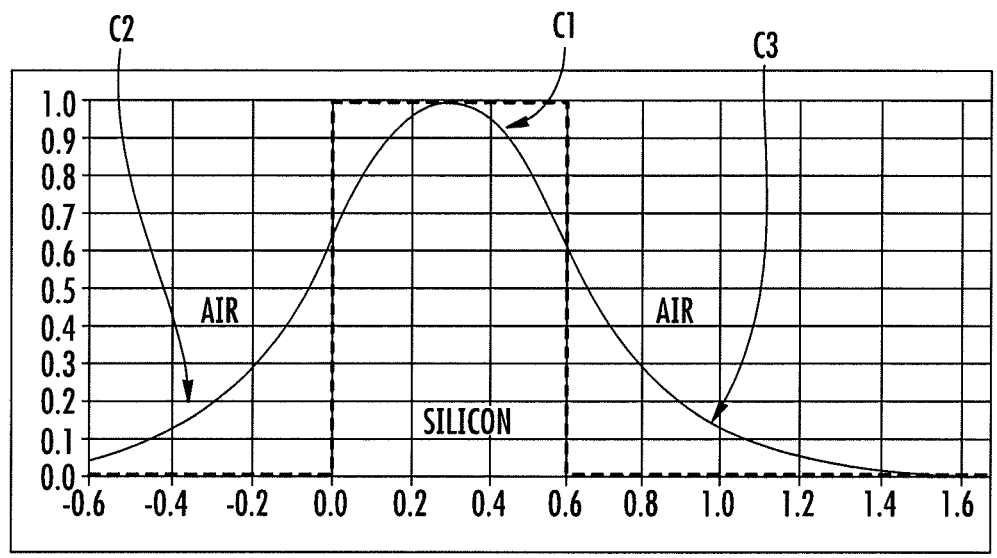
FIG. 4 illustrates the variation in the amplitude of the electromagnetic wave inside and around a movable element of the device according to the invention, placed in the air and made of silicon.

FIG. 4 illustrates the variation in the amplitude of the normalized electromagnetic field as a function of the position relative to the movable element 11.

This movable element is made of silicon and has a thickness of 0.6 μm. The variation in the amplitude of the field within the movable element corresponds to the portion C1 of the curve shown. The variation in the amplitude of the electromagnetic field close to each of the faces of the element 11 is shown by the curved portions C2 and C3.

Thus, FIG. 4 shows the benefit of having a movable element of reduced thickness. Specifically, as this thickness is reduced, the amplitude of the field close to the element 11 is increased and can therefore serve to excite the molecules of the gas that it is desired to detect. The precision obtained will therefore be increased.

As a variant, one of the faces of the movable element 11 may be coated with a layer having an index lower than that of silicon, and preferably an index close to that of air.

Thus, on a strip-type element made of silicon having a thickness of 0.6 µm, a silica layer of 0.5 µm thickness may be provided on one of its faces, for example the face 112.

Figure 5:
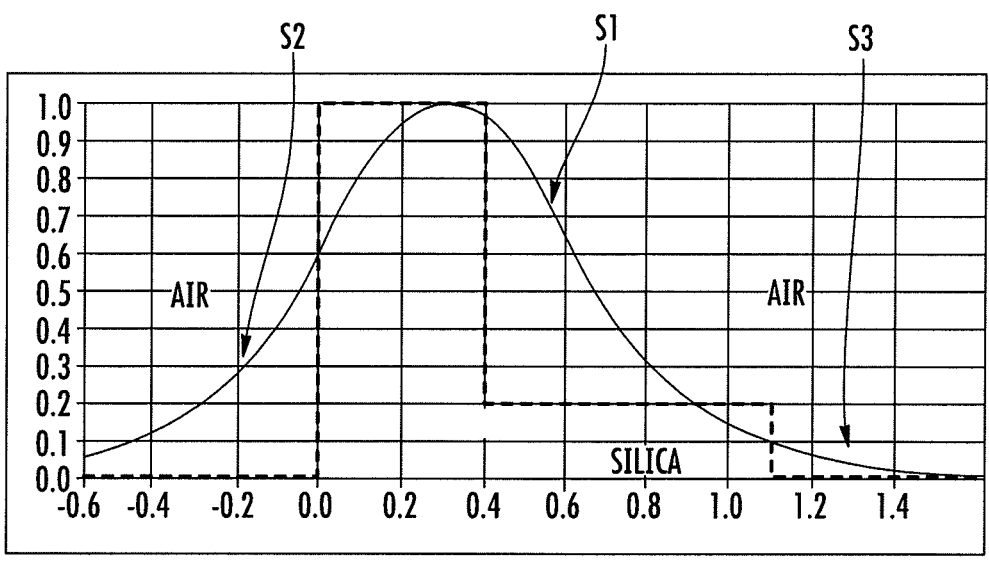
FIG. 5 illustrates the variation in the amplitude of the electromagnetic wave inside and around a movable element of the device according to the invention, placed in the air, made of silicon and coated on one of its faces with a layer of silica.

The distribution of the electromagnetic field within the element 11 and on either side of this element is illustrated in FIG. 5.

Thus, the curve S1 shows the variation in the amplitude of the electromagnetic field within the silicon part (from 0 to 0.6 µm) and then in the silica part (from 0.6 to 1.1 µm).

The curve S2 shows the variation in the amplitude of the electromagnetic field in a zone extending away from the silicon face of the element 11 (from 0 to −0.6 µm), whereas the curve S3 shows the variation in the amplitude of the electromagnetic field on moving away from the silica face of the movable element (from 1.1 to 1.5 µm).

In this alternative embodiment, an asymmetry is introduced into the element 11. Thus, the electromagnetic field that develops close to the silicon face has a higher intensity than that developed close to the silica face, the field being more intense on the side of the environment having the highest index.

In particular, it may be noted that the amplitude of the electromagnetic field on the silicon surface of the element 11 is about 6 times higher than the amplitude of this field on the silica face of the element 11.

Consequently, the intensity of the electromagnetic field is about 36 times higher on the surface of the silicon than on the surface of the silica.

Thus, it is essentially the gas molecules on the silicon layer side of the element 11 that will be excited. This enables the sensitivity of the measurement to be increased by promoting impacts of the excited molecules on at least one of the two faces of the element 11.

However, it should be noted that the detection device according to the invention is effective even if no asymmetry is introduced into the structure of the strip-type element. This is because the density of the gas around this element is not homogenous.

The width l of the waveguide 1 may be between 1 and 10 µm, preferably between 1 and 2 µm, in the first part 10 and between 0.6 and 2 µm in the element 11. FIG. 2 illustrates a waveguide having the same width in both the first and second parts 10 and 11.

Moreover, its length L may be between 10 and 500 µm, preferably between 10 and 100 µm.

The width and the length of the waveguide are independent of the wavelength of the gas to be detected.

However, for a single-mode waveguide, the width may be close to the wavelength. In this case, the wave is transversely polarized.

In general, the ratio L/l, is at least equal to 10.

It will be understood that the length of the element 11 determines its flexibility or its capability to vibrate.

However, the length is limited by the mechanical strength requirement of the strip.

Thus, in another embodiment, the far end 111 is not free as illustrated in FIGS. 1 and 2, but connected to the support and especially to the layer 31.

In this alternative embodiment, the element 11 is therefore fixed at both its near and far ends. This allows the length of the element to be increased.

Another alternative embodiment is illustrated in FIG. 3.

In this embodiment, a slot 113 is formed in the element 11 close to its near end 110.

This slot is formed so as to be approximately transverse to the direction in which the element 11 extends.

It allows the element 11 to be made more flexible and therefore set into vibration more easily.

When the element 11 is fixed at both its ends, such a slot may advantageously be provided at its near and far ends.

The above description shows that the gas detection device is particularly compact since, on the one hand, the waveguide acts both as excitation means and as means for detecting the heat-up of the gas and, on the other hand, the vibration measurement sensor is close to the waveguide.

The detection device will be more sensitive the larger the area L.l of the element 11 and the smaller the thickness e.

Moreover, the detection device may be placed directly in the environment containing the gas which it is desired to detect, without requiring ancillary means such as pumping means for circulating the gas. This device may therefore be easily used in domestic applications.

Alternative embodiments may be envisaged for increasing the power of the gas excitation means and for thus increasing the sensitivity of the device.

Thus, the power can be conventionally increased by a structured mirror on the waveguide (a Bragg mirror) placed after the movable element so as to reflect the light flux into it and thus double the excitation power.

Figure 6:
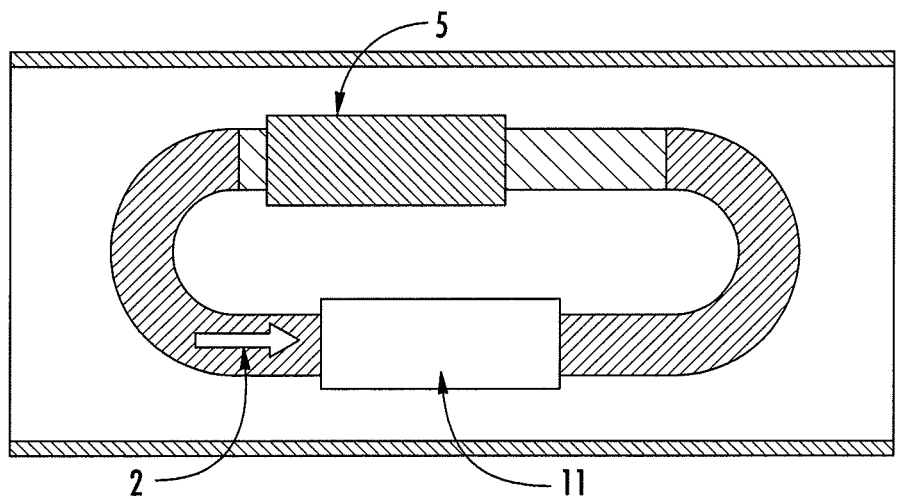
FIG. 6 illustrates an alternative embodiment of the detection device according to the invention, showing a particular arrangement of the gas excitation means and of the movable element of the detection device.
Figure 7A:
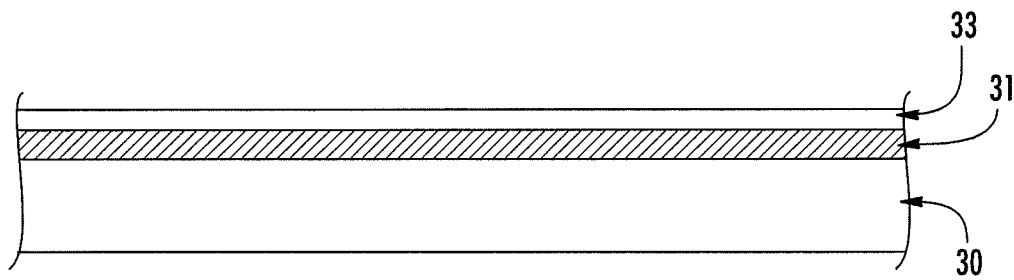
FIGS. 7a to 7d represent four steps of a process for producing an example of a gas detection device according to the invention.
Figure 7B:
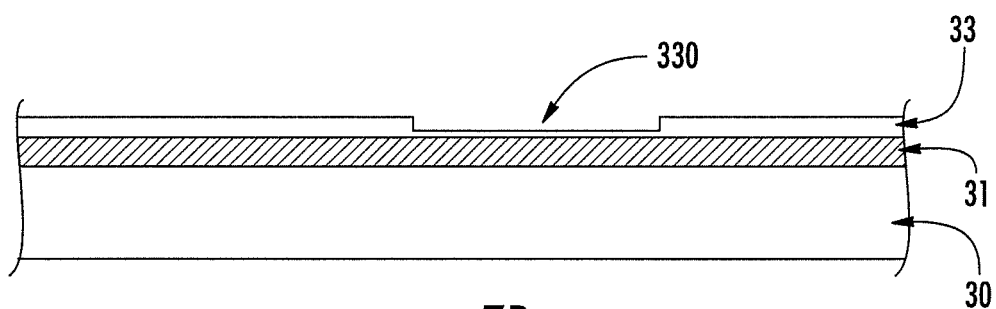
Figure 7C:
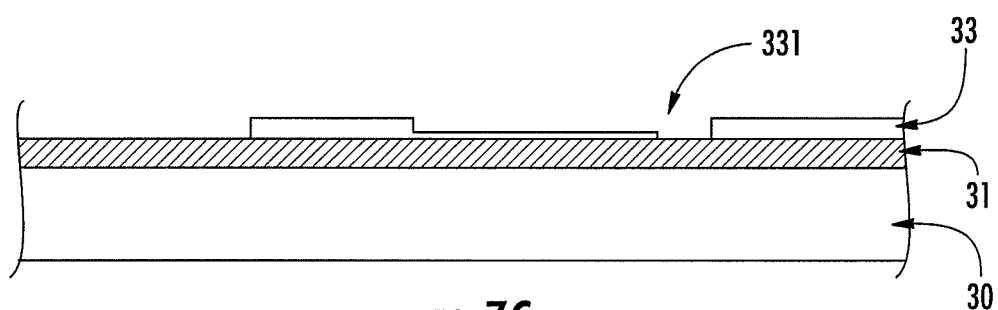
Figure 7D:
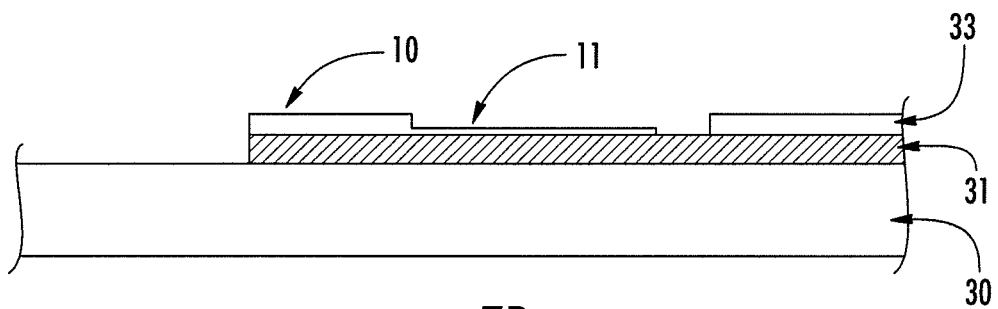

FIG. 6 illustrates a ring laser cavity, the reference 5 illustrating the laser gain medium and the reference 11 corresponding to the movable element of the detection device.

The laser power may be increased by a factor of 2, or even by a greater factor, for example between 10 and 100, by thus making the electromagnetic wave circulate several times in the movable element.

This particular arrangement of the laser source enables the laser power in the movable element 11 to be increased by operating in what is called "multipass" mode.

This increase in the power of the electromagnetic wave makes it possible to increase the sensitivity of the detection device according to the invention without increasing the laser power of the source.

Again, with the aim of increasing the sensitivity of the device, it is conceivable to modulate the electromagnetic excitation at a multiple or submultiple frequency of that of the natural resonance of the movable element 11, that is to say at the eigen frequencies of the movable element. This enables the resonance amplitude to be exaggerated by a cumulative resonant excitation process. The detection may be enhanced by synchronous detection.

If the environment contains several different gases that have to be detected, it is conceivable to operate several detection devices as described above in parallel, the structure of each of them being adapted to one of the gases to be determined.

In another embodiment, the various gases present in the environment are detected in succession with a single detection device by using a tunable laser source, the wavelength of which is adjusted to each detection.

Referring now to FIGS. 7a to 7d, these describe four steps of a method for obtaining a detection device according to the invention of the type illustrated in FIGS. 1 and 2.

The first step (FIG. 7a) of the method consists in producing a stack of three successive layers: a silicon layer 30, a silica layer 31 and a silicon layer 33.

Such a stack is suitable for producing a $CO_2$ detection device, this device operating with an electromagnetic wave having a wavelength of about 4.2 µm.

In this case, the thickness of the silica layer 31 is typically between 1 and 10 µm, whereas the thickness of the silicon layer 33 is between 1 and 2 µm. As indicated above, the silicon layer may be coated with a silica cladding.

The next step (FIG. 7b) consists of a photolithography and etching step carried out on the silicon layer 33 so as to thin it in the region 330.

In this zone 330, the thickness of the silicon layer will be between 0.1 and 1 µm, for example equal to 0.6 µm.

The next step (FIG. 7c) of the method is a photolithography and etching step, whereby the silicon layer 33 is completely removed in a zone 331 located at the end of the zone 330.

The final step (FIG. 7d) consists in carrying out wet, reactive ion or vapour phase etching so as to remove the silica layer 31 beneath the zones 330 and 331, optionally through a lithographic mask.

These various steps serve to obtain the two parts 10 and 11 of the waveguide, the thicknesses of which are differentiated, and to free the part 11 of the waveguide from the stack formed by the layers 30 and 31. The element 11 is thus able to move and can vibrate because of the impact of the gas molecules on its faces.

Of course, similar methods could be used to produce structural variants of the detection device according to the invention.

Moreover, the method may be used to produce the sensor 4, designed to measure the vibration of the element 11, directly on the silicon layer.

In this regard, the reader may again refer to the article by C. Hagleitner et al.

The reference signs inserted after the technical features in the claims have the sole purpose of making it easier for them to be understood and in no way limit the scope thereof.

The invention claimed is:

1. Device for detecting a gas, comprising:
   excitation means, for exciting said gas by means of an electromagnetic wave having a wavelength corresponding approximately to that of said gas; and
   detection means, for detecting the excitation of said gas, characterized in that the device comprises:
   a waveguide connected to said excitation means, a part of which forms a movable element configured to be in contact with said gas and capable of being set into vibration by the impact of the excited gas molecules; and
   a measurement sensor for measuring the vibration of said element, said measurement sensor and said element forming said detection means.

2. Device according to claim 1, in which the movable element is of the strip type.

3. Device according to claim 2, in which the movable element is of the comb type.

4. Device according to one of claim 1, characterized in that said element is cantilevered at a near end thereof, and a far end thereof being free.

5. Device according to one of claim 1, characterized in that the near end of said element and said far end of the element are held fixed.

6. Device according to claim 4, characterized in that said element includes, close to said near end and/or said far end, a slot extending approximately transversely.

7. Device according to claim 1, characterized in that a thickness ($e_1$) of the element is less than a thickness ($e_2$) of the rest of the waveguide.

8. Device according to one of claim 1, characterized in that the waveguide is made of a single material.

9. Device according to claim 8, characterized in that said element has, on a face thereof, a layer of a material having an index of refraction lower than that constituting the waveguide.

10. Device according to one of claim 1, characterized in that the gas excitation means are formed by a laser.

11. Device according to claim 10, characterized in that the laser includes a laser cavity which is a ring laser cavity, and wherein the waveguide is placed inside the laser cavity.

* * * * *